(12) United States Patent
Neidert et al.

(10) Patent No.: US 8,262,672 B2
(45) Date of Patent: Sep. 11, 2012

(54) MEDICAL DELIVERY DEVICE CONSTRUCTION

(75) Inventors: Michael R. Neidert, Co. Galway (IE); Kenneth C. Gardeski, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 819 days.

(21) Appl. No.: 12/424,100

(22) Filed: Apr. 15, 2009

(65) Prior Publication Data
US 2009/0264862 A1 Oct. 22, 2009

Related U.S. Application Data

(60) Provisional application No. 61/045,392, filed on Apr. 16, 2008.

(51) Int. Cl.
*A61F 11/00* (2006.01)
*A61M 5/178* (2006.01)
*A61M 25/00* (2006.01)
*A61B 5/00* (2006.01)

(52) U.S. Cl. .................. 606/108; 604/164.05; 604/523; 600/585

(58) Field of Classification Search .................. 606/108, 606/184; 604/164.01–164.11, 523; 600/585
See application file for complete search history.

(56) References Cited

U.S. PATENT DOCUMENTS
8,192,477 B2 * 6/2012 Mertens et al. .............. 623/1.11
2004/0097965 A1 5/2004 Gardeski et al.

FOREIGN PATENT DOCUMENTS
WO 9703810 2/1997
WO 03008018 1/2003

* cited by examiner

Primary Examiner — Gary Jackson
Assistant Examiner — Michael Mendoza

(57) ABSTRACT

A delivery device includes an outer sidewall and an inner sidewall extending therein. An outer surface of the inner sidewall defines a plurality of longitudinally extending grooves, each of which interlock with a corresponding inward protruding member of a plurality of longitudinally extending inward protruding members defined by an inner surface of the outer sidewall. A longitudinally extending lumen of the device, which may accommodate delivery of an implantable medical device, is defined, at least in part, by the inner surface of the inner sidewall. A slitting zone of the device, for example, provided by one of the sidewalls extending less than 360 degrees about a longitudinal axis of the device, enables removal of the delivery device from around the delivered device.

4 Claims, 7 Drawing Sheets

MEDICAL DELIVERY DEVICE CONSTRUCTION

CROSS-REFERENCE TO RELATED APPLICATION

This application claims the benefit of U.S. Provisional Application No. 61/045,392 filed on Apr. 16, 2008. The disclosure of the above application is incorporated herein by reference.

TECHNICAL FIELD

The present disclosure relates to medical delivery devices, for example, sheaths and/or catheters, and more particularly to constructions of delivery devices, which constructions facilitate the removal of the devices following delivery therethrough of implantable medical devices.

BACKGROUND

Many medical devices, for example, medical electrical leads and drug delivery catheters, include elongate bodies facilitating therapy delivery and/or diagnostic sensing; the bodies often include lumens extending along a longitudinal axis thereof. Such a lumen may provide a passageway for a stylet or guidewire that helps to guide the device to a target site within a body of a patient, for example, within a chamber of the heart. In recent years, the space used for guidewire/stylet lumens within elongate bodies of many medical devices has either been eliminated, to downsize the device bodies, or used for other purposes, for example, for the routing of one or more additional lead wires that add functionality to the device. Delivery devices, such as catheters, have been developed to guide these elongate medical devices, which do not have stylet/guidewire lumens, to a target implant site.

In order to implant the elongate body of a medical device in the venous system of a patient, for example, a right atrium, a right ventricle or a coronary sinus, an implanting physician may first obtain venous access by inserting an introducer sheath into an access site, for example, in the cephalic, subclavian, or axillary vein, according to methods known to those skilled in the art. The implanter may then pass a medical device into the venous system via insertion within a delivery catheter lumen, either before or after inserting the delivery catheter into the venous system through the introducer sheath. In some cases, the delivery catheter may also serve as the introducer sheath. Once the delivery catheter has been steered or directed to a target implant site within the venous system, the implanter may advance the medical device out through a distal opening of the lumen and then fix a distal end of the device at the site. After the medical device is fixed, the implanter may remove the introducer sheath and/or the catheter, from the venous system, by splitting a wall thereof to peel the sheath and/or catheter away from around a proximal portion of the medical device body that extends out from the venous system. This type of removal is desirable if the proximal portion, remaining outside the patient's venous system, is too large to fit within the delivery lumen of the sheath/catheter and/or if the implanter would prefer to maintain direct contact with the proximal portion of the implanted device while removing the sheath/catheter.

For many types of delivery catheters and introducer sheaths, a special slitting tool, that includes a cutting edge, is required to slit through a sidewall of the catheter/sheath, in order to remove the catheter/sheath from around the implanted device body. For those catheters and sheaths which have sidewalls constructed to provide kink resistance and adequate torque and push transfer, for steering the delivery catheter to the target site, slitting with these tools can be somewhat challenging. Even if a catheter/sheath sidewall is amenable to slitting, it may be difficult, particularly if the catheter/sheath is relatively long, to pull the catheter/sheath against the cutting edge of the slitting tool, along a relatively straight line in order to avoid a spiraling cut that could cause the peeling away of the sheath/catheter sidewall to dislodge the implanted device. Thus, there is a need for new delivery device constructions having kink-resistant sidewalls, that are sufficiently stiff to provide push and torque transfer, and that also include features to accommodate slitting.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present disclosure. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1A:
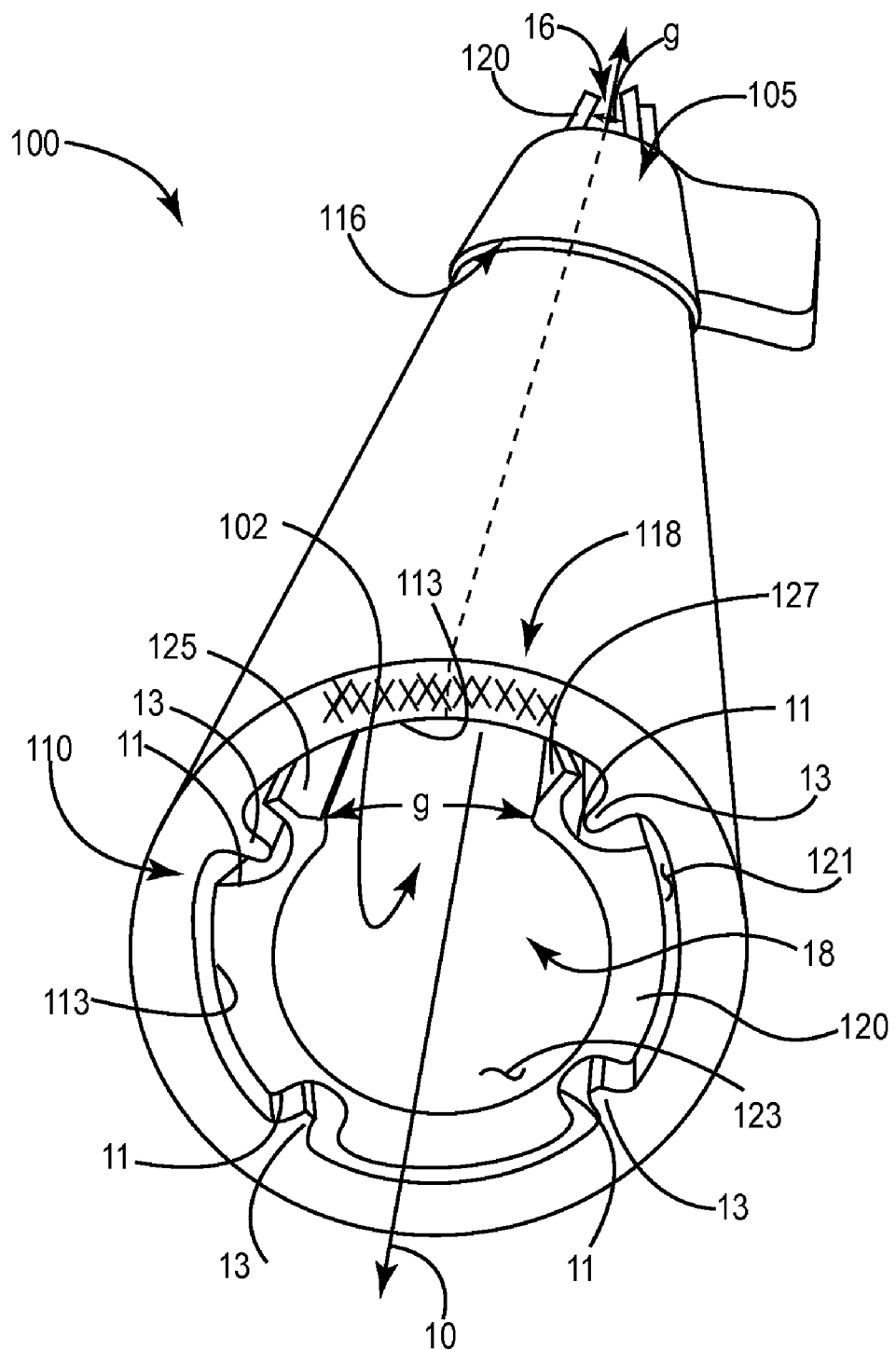
FIG. 1A is a perspective view of a delivery device.

FIG. 1A is a perspective view of a delivery device 100. FIG. 1A illustrates device 100 including an outer sidewall 110 surrounding an inner sidewall 120. Outer sidewall 110 is shown extending longitudinally from a proximal end 116 to a distal end 118 thereof, and extending 360 degrees about a longitudinal axis 10 of device 100; and inner sidewall 120 is shown extending within outer sidewall 110, between proximal end 116 and distal end 118, and extending about axis 10, from a first end 125 of sidewall 120 to a second end 127 of sidewall 120, less than 360 degrees, such that a portion of an inner surface 113 of outer sidewall 110 spans a longitudinally extending gap g between first and second ends 125, 127. According to the illustrated embodiment, an inner surface 123 of inner sidewall 120 and the portion of inner surface 113 of outer sidewall 110, which spans gap g between first and second ends 125, 127 of inner sidewall 120, together define a longitudinally extending lumen 102 of device 100. According to preferred embodiments, lumen 102 of delivery device 100 accommodates passage therethrough of an implantable device, such as a medical electrical lead. The implantable device may be inserted into lumen 102 at a first opening 16, in proximity to proximal end 116, and pushed out through a second opening 18 of lumen 102, in proximity to distal end 118.

FIG. 1A further illustrates inner sidewall 120 including a plurality of longitudinally extending grooves 11, which are defined by an outer surface 121 of inner sidewall 120, and which interlock with a plurality of longitudinally extending and inward protruding members 13 of outer sidewall 110, which are defined by inner surface 113 of outer sidewall 110. Each of sidewalls 110, 120 may be individually formed, via extrusion, from a medical grade polymer; a particular material, or material combination, selected for each sidewall 110, 120 provides delivery device 100 with adequate stiffness for push and torque transfer, in conjunction with enough flexibility to be kink-resistant when traversing one or more bends along a pathway for delivering the implantable device to a target implant site. Some exemplary material combinations will be described below.

According to certain embodiments, device 100 further includes a lubricious coating or layer, for example, Dow MDX4-4195 reactive silicone lubricant, extending over inner surface 123 of inner sidewall 120 and, at least, over the portion of inner surface 113 of outer sidewall 110, which spans gap g, in order to minimized friction between lumen 102 and an implantable device being delivered therethrough. As an alternative to a lubricious coating, one or both of sidewalls 110, 120 may be formed, at least in part, from a material that is inherently lubricious, for example, a fluoropolymer.

Sidewalls 110, 120 may be joined together solely via the illustrated interlocking, or may be further joined together, for example, via adhesive or thermal bonding, according to methods, known to those skilled in the art, which are appropriate for the materials forming sidewalls 110, 120. Some suitable adhesives include, without limitation, UV curable adhesives, cyanoacrylate, and polyurethane adhesives. But, because of the interlocking construction of device 100, materials for sidewalls 110, 120 need not be selected based on bonding compatibility. According to exemplary embodiments of the present invention, suitable materials for outer sidewall 110 include without limitation, polyether block amides, such as PEBAX®, nylons (PA, such as polyamide-12 (PA-12) or polyamide-6 (PA-6), silicone rubbers, polyurethanes (PU), polyethylenes and polyesters, such as polybutylene terephthalate (PBT), and suitable materials for inner sidewall 120 include without limitation, polyether block amides, such as PEBAX®, polyethylenes (PE), such as high density polyethylene (HDPE) or linear low density polyethylene (LLPE), polyetheretherketones (PEEK), fluoropolymers, such as polytetrafluoroethylene (PTFE), thermoplastic fluoropolymers, such as polyvinylidene difluoride (PVDF), nylon (PA), and polyimide (PI). As mentioned above, preferred combinations of the above referenced materials, some examples of which are listed in TABLE 1, below, provide delivery device 100 with adequate stiffness for push and torque transfer, in conjunction with enough flexibility to be kink-resistant.

TABLE 1

| Outer sidewall | Inner sidewall |
| --- | --- |
| PEBAX ® | PEBAX ® |
| PU | PTFE |
| PBT | PVDF |
| PA | PE |

With reference to FIG. 1A, it may be appreciated that a segment of outer sidewall 110, which is demarcated with cross-hatching and which corresponds to the portion of inner surface 113 spanning gap g, forms a slitting zone, which may be slit with a slitting tool, for example, along the dotted line, to remove delivery device 100 from around the implantable device after the implantable device has been delivered and implanted at the target site. Thus, gap g need only be wide enough to allow passage of a cutting edge of known slitting tools therebetween. FIG. 1 further illustrates device 100 including a hub 105, which may be grasped by a user during slitting, and inner sidewall 120 extending proximally from hub 105, for example, to provide an exposed portion of gap g as a guide for slitting. It should be noted that, in alternate embodiments, sidewall 120 does not extend as illustrated and is completely contained within outer sidewall 110 and hub 105. Furthermore, it should be noted that hub 105 need not extend over the slitting zone as is shown in FIG. 1A.

A variety of slitting tools and methods for using these tools to slit catheters and sheaths are well known to those skilled in the art. According to exemplary embodiments of the present invention, a width of gap g is between approximately 0.01 inch and approximately 0.05 inch. For a larger width of gap g, the corresponding segment of outer sidewall 110 (cross-hatched) may include a stiffening insert, which does not frustrate slitting but helps to prevent buckling of that segment of sidewall 110, which is not reinforced by inner sidewall 120, as device 100 is manipulated to deliver an implantable device. Alternately, or additionally, inner sidewall 120 does provide some reinforcement across gap g, for example, as illustrated in FIG. 1B.

Figure 1B:
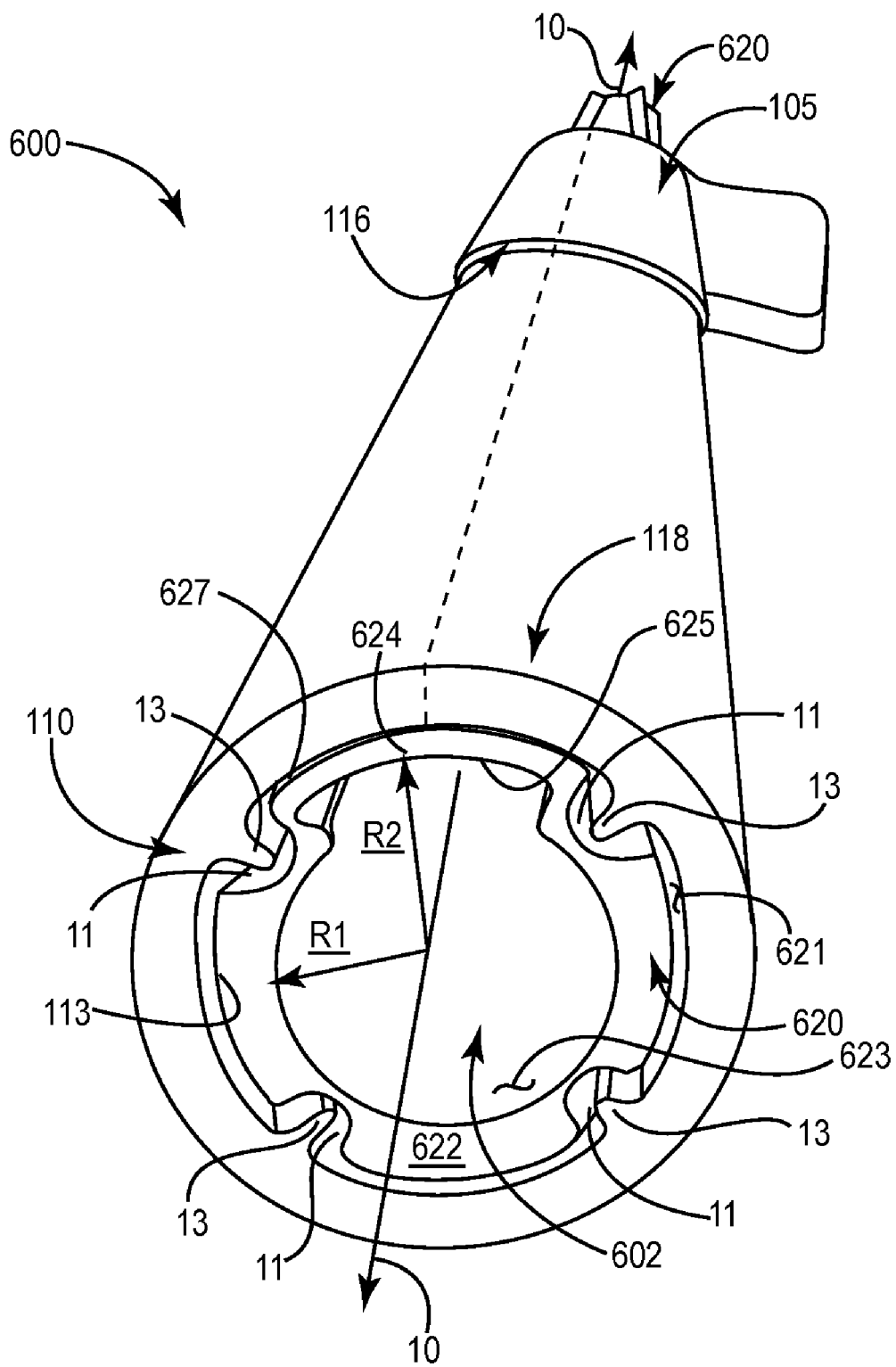
FIG. 1B is a perspective view of a delivery device.

FIG. 1B is a perspective view of a delivery device 600, according to some other embodiments. FIG. 1B illustrates device 600 including outer sidewall 110, similar to device 100, as previously described, and an inner sidewall 620, which, unlike inner sidewall 120 of device 100, extends about axis 10 360 degrees. Inner sidewall 620 is shown including a first segment 622 extending greater than 270 degrees about axis 10 and a second segment 624 extending less than 90 degrees about axis 10; first segment 622 includes an outer surface 621 defining grooves 11, which, similar to inner sidewall 120 of device 100, interlock with inward protruding members 13 of outer sidewall 110. FIG. 1B further illustrates an inner surface 623 of first segment 622 defining a first radius R1 of a lumen 602 of device 600, and an inner surface 625 of second segment 624 defining a second radius R2 of lumen 602, which second radius R2 is greater than first radius R1. Like lumen 102 of device 100, lumen 602 extends from an opening in proximity to proximal end 116 of outer sidewall 110 to an opening in proximity to distal end 118 of outer sidewall 110, for example, to provide passage for delivery of an implantable device. Although FIG. 1B shows inner sidewall 620 extending proximally from hub 105, the invention is not so limited, and inner sidewall 620 may be contained between hub 105 and distal end 118 of outer sidewall 110.

According to the illustrated embodiment, second segment 624 of inner sidewall 620 has a wall thickness which is less than a wall thickness of portions of first segment 622 that extend between each groove 11, and further includes an outer surface 627 extending in close proximity to an adjacent portion of inner surface 113 of outer sidewall 110, such that a contour of segment 624 closely matches that of inner surface 113. Thus, second segment 624 may provide additional support to a slitting zone of device 600, generally indicated by the dotted line in FIG. 1B, without significantly increasing a force required to slit, for example, as compared to that for device 100. Suitable materials for each of sidewalls 110 and 620, of device 600, may be selected from the groups of exemplary materials indicated above for device 100; according to some exemplary embodiments, both outer and inner sidewalls 110, 620 are formed from PEBAX®.

Figure 2A:
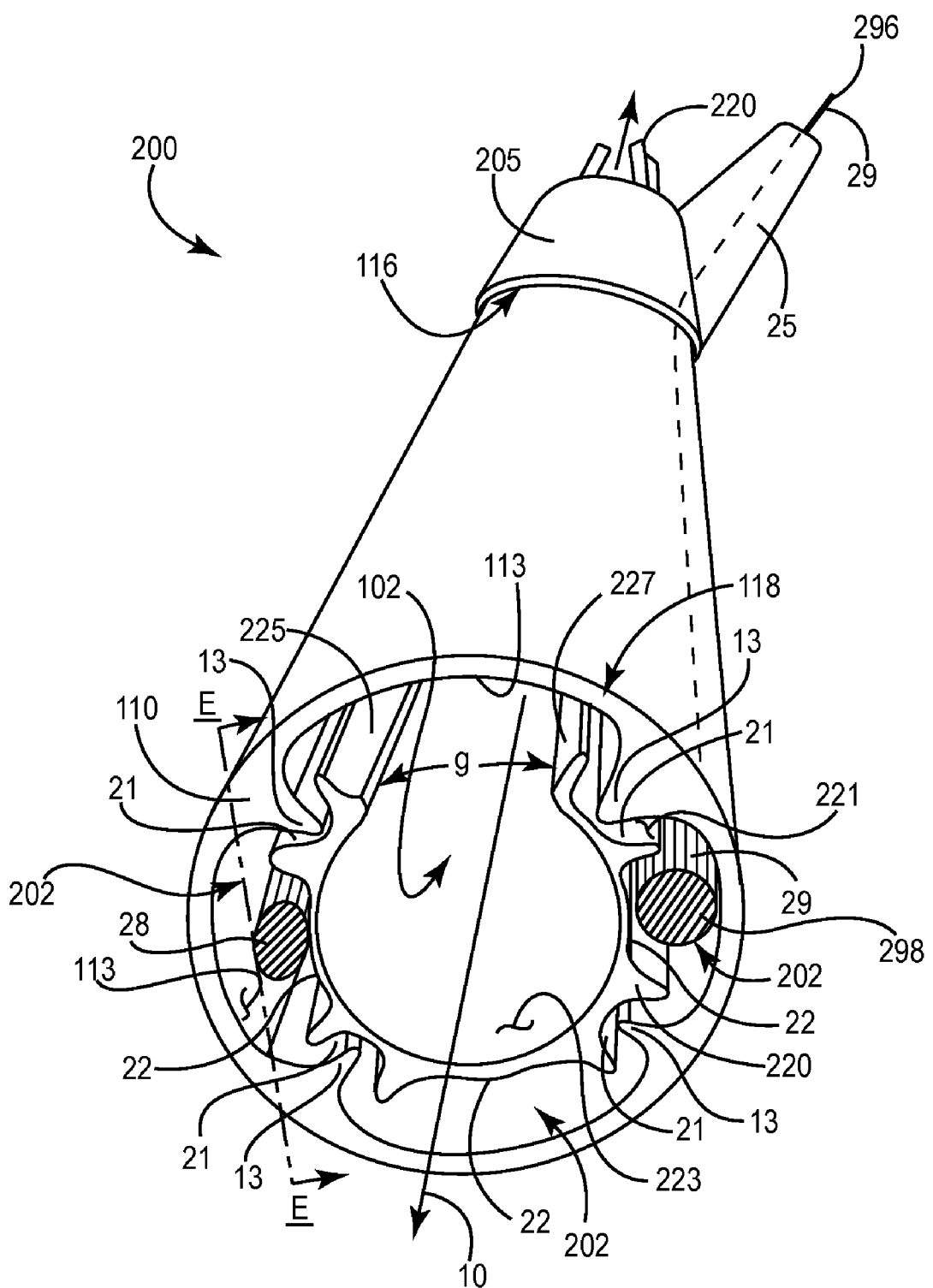
FIG. 2A is a perspective view of a delivery device.

FIG. 2A is a perspective view of a delivery device 200, according to some alternate embodiments of the present invention. FIG. 2A illustrates device 200 including an inner sidewall 220 extending within outer sidewall 110, between proximal and distal ends 116, 118, and about axis 10, from a first end 225 of inner sidewall 220 to a second end 227 of inner sidewall 220, less than 360 degrees. Similar to device 100, device 200 further includes lumen 102, which is defined by an inner surface 223 of inner sidewall 220 and a portion of inner surface 113 of outer sidewall 110 that spans longitudinally extending gap g, which gap g is between ends 225, 227 of inner sidewall 220, similar to that between ends 125, 127 of sidewall 120 of device 100. Like device 100, the construction of device 200, employing sidewalls 110, 220, provides adequate stiffness, for push and torque transfer, in conjunction with enough flexibility to be kink-resistant for delivering the implantable device to a target implant site, while also facilitating a slitting of device 200. Inner sidewall 220 is also shown extending proximally from hub 205, similar to inner sidewall 120 of device 100, and like the aforementioned alternate embodiments of device 100, sidewall 220 may alternately be contained between hub 205 and distal end 118 of outer sidewall 110, according to alternate embodiments of device 200.

FIG. 2A further illustrates an outer surface 221 of inner sidewall 220 defining a first plurality of grooves 21, each of which interlock with a corresponding protruding member 13 of outer sidewall 110, and a second plurality of grooves 22, which, together with other portions of inner surface 113 of outer sidewall 110, define a plurality of additional longitudinally extending lumens 202. According to the illustrated embodiment, any of lumens 202 may be used to contain another member of device 200, for example, a passive or active conductor coupled to an electrode or sensor (not shown) of device 200, or a pull wire to steer a tip of device 200, or members to tailor a stiffness along a length of device 200, as will be described below. Any of lumens 202 may additionally or alternately be used for passage of another device or medium therethrough, from one of ends 116, 118 to the other, for example, a delivery wire 29, as shown in FIG. 2A, or a fluid, which will be described in conjunction with FIG. 3.

FIG. 2A shows delivery wire 29 having a proximal end 296, which extends proximally from a side port 25 of a hub 205 of device 200, and a distal end 298, which is approximately aligned with distal end 118 of outer sidewall 110. According to some embodiments of the present invention, delivery wire 29 is like a guidewire, having a relatively floppy or atraumatic distal tip, so that distal end 298 may be advanced distally out in front of delivery device 200 to provide a tracking path for device 200, according to over-the-wire delivery methods, which are well known to those skilled in the art. According to alternate embodiments, delivery wire 29 is more like a stylet whose distal end 298 would be contained within outer sidewall 110, either via a length limitation on delivery wire 29 or by a sealing, or closing off of the corresponding lumen 202 at distal end 118. Either type of delivery wire 29 may be pre-formed into a pre-determined curvature prior to insertion into the corresponding lumen 202, in order to impart a shape to delivery device 200, which shape may facilitate advancement of delivery device 200 to the target implant site. According to some embodiments, a lubricious coating, or layer, extends over surface 113 and 221, at least those portions forming lumens 202, to facilitate 'smooth' passage of delivery wire 29 therethrough. Lubricious surfaces 113, 221 may also be desired to aid in assembling sidewalls 110, 220 together, to form device 200 (and/or to separate sidewalls 110, 220 from one another). In this light, interfacing surfaces of any of the delivery devices described herein may include a lubricious coating, to aid in the assembly of the devices.

Although three of lumens 202 are shown in FIG. 2A, the invention is not so limited, and it may be appreciated that any number of additional lumens 202 may be formed by alternate configurations of inner sidewall outer surface 221, for example, configurations that define an alternate number of grooves 22, and/or by alternate configurations of outer sidewall inner surface 113, for example, configurations that define additional inward protruding members 13, which alternative configurations are all within the scope of the present invention. According to some embodiments, inner sidewall 220 is bonded to outer sidewall 110 at each interface between inward protruding members 13 and grooves 21; the bonding may extend along an entire length of outer sidewall 110 in order to seal lumens 220, 102 from one another along the length.

With reference to FIG. 2A, it should be understood that side port 25 of hub 205, in proximity to proximal end 116, is in fluid communication with the lumen 202, in which delivery wire 29 is shown extending. Although not shown, it should be understood that device 200 may include one or more additional ports, each additional port corresponding to the other of lumens 202; each other lumen 202 of device 200 may include a proximal and/or distal port. Although not shown, an inflatable member may be joined to outer sidewall 110, a port formed in sidewall 110 between the inflatable member and one of lumens 202, and a distal end of that lumen 202 sealed off so that an inflation medium may be injected through the lumen 202, for example, at side port 25 of hub 205, in order to inflate the inflatable member. Those skilled in the art will appreciate, that the inflatable member may be used to block blood flow within a vessel so that a contrast medium may be injected into the vessel, downstream of device 200, for example, through lumen 102, or through any of the other lumens 202, in order to visualize, via fluoroscopy, a navigation pathway for device 200 through the vessel.

Figure 2B:
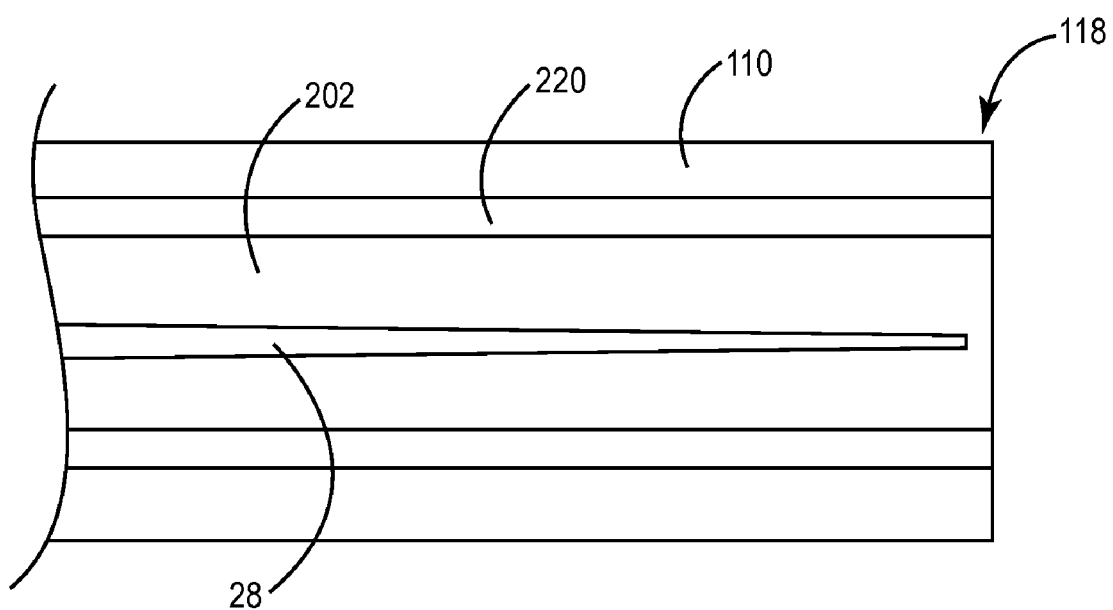
FIG. 2B is a section view through section line E-E of FIG. 2A.

According to further embodiments, one or more elongate stiffening members may be enclosed in any or all of lumens 202; in some embodiments the one or more members extend only in proximity to proximal end 116, while in other embodiments the members extend from proximal end 116 to distal end 118 and are tapered or spiral cut in proximity to distal end 118 in order to create a variable stiffness along the length of device 200. FIG. 2A shows a stiffening member 28 extending within one of lumens 202, and FIG. 2B, which is a section view through section line E-E of FIG. 2A, shows member 28 being tapered for reduced stiffness in proximity to distal end 118, according to some embodiments. Alternately or additionally, variable stiffness may be achieved by varying a thickness or material properties of either or both of sidewalls 110, 220 along the lengths thereof. Suitable materials for each of sidewalls 110 and 220, of device 200, may be selected from the groups of exemplary materials indicated above for device 100; according to some exemplary embodiments, both outer and inner sidewalls 110, 220 are formed from PEBAX®, various durometers of which may be employed, in some embodiments, to vary the stiffness of sidewalls 110, 220 along the length thereof.

Figure 3:
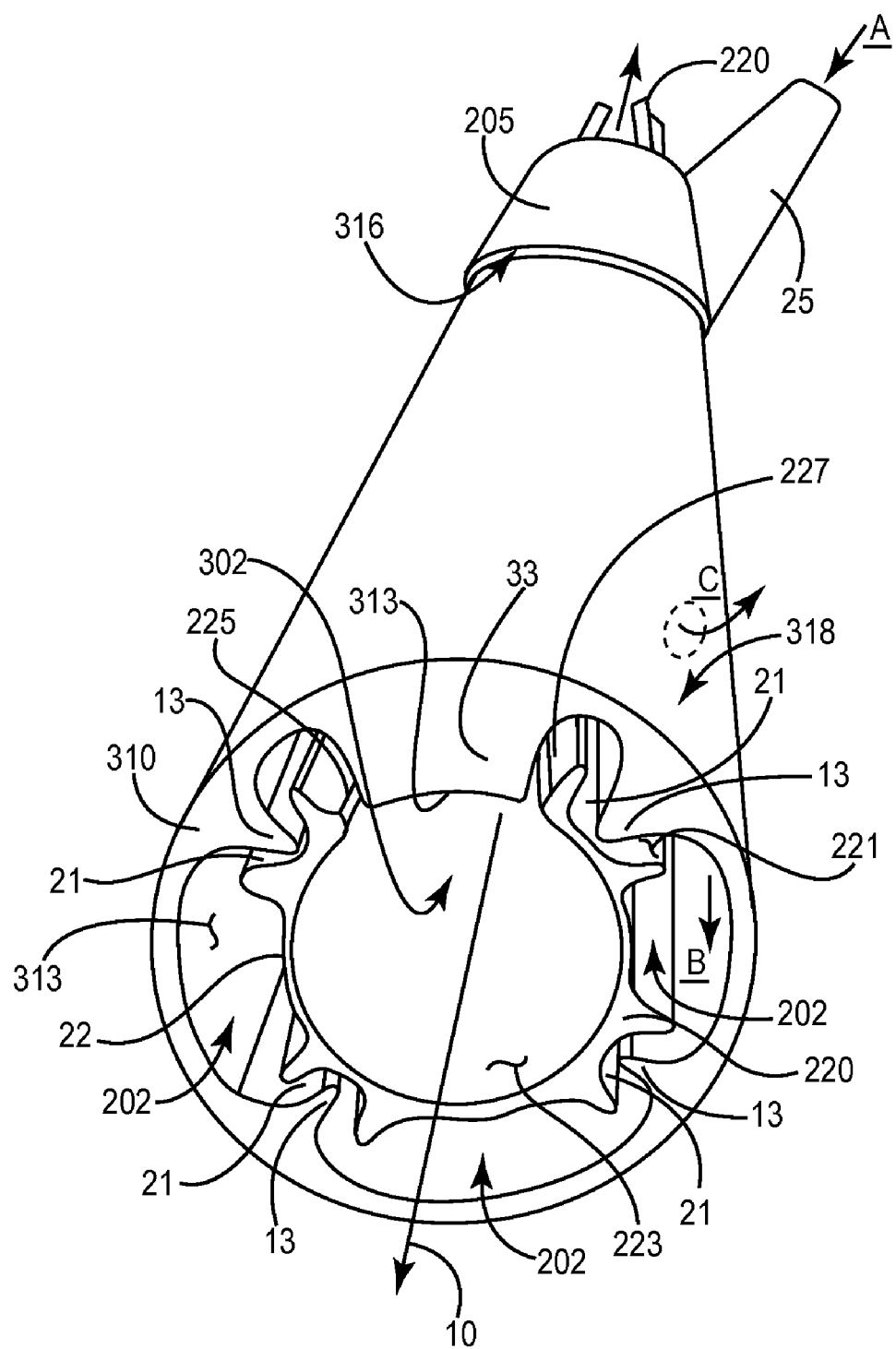
FIG. 3 is a perspective view of a delivery device.

FIG. 3 is a perspective view of a delivery device 300, according to other alternate embodiments. FIG. 3 illustrates device 300 including inner sidewall 220 extending within an outer sidewall 310, between proximal and distal ends 316, 318 of outer sidewall 310, and about axis 10, between first and second ends 225, 227, less than 360 degrees. Similar to device 200, grooves 21 of inner sidewall 220 interlock with inward protruding members 13 of outer sidewall 310, and device 300 further includes lumens 202 defined by grooves 22 of sidewall 220 and portions of an inner surface 313 of outer sidewall 310. In contrast to device 200, inner surface 313 of outer sidewall 310 of device 300 defines an additional longitudinally extending and inward protruding member 33, which extends in between ends 225 and 227 of inner sidewall 220. According to the illustrated embodiment, inner surface 223 of inner sidewall 220, along with a portion of inner surface 313 of outer sidewall 310, which portion extends along an inward directed face of inward protruding member 33, defines a lumen 302 of delivery device 300, which lumen 302 accommodates passage of an implantable device therethrough. Suitable materials for each of sidewalls 310 and 220, of device 300, may be selected from the groups of exemplary materials indicated above for device 100; according to some exemplary embodiments, both outer and inner sidewalls 310, 220 are formed from PEBAX®.

FIG. 3 further illustrates one of lumens 220 in fluid communication with side port 25 of hub 205, for delivery of a fluid, which is injected, per arrow A, into side port 25. The injected fluid may be a therapeutic agent, for example, a drug, or a diagnostic agent, for example, a radiopaque contrast agent. According to some embodiments, the injected fluid exits device 300 in proximity to distal end 318, for example, per arrow B. According to some alternate embodiments, the injected fluid exits delivery device 300 via a port (shown with dashed lines in FIG. 3) extending through outer sidewall 310, for example, per arrow C. An inflatable member, for example, as previously described, may be joined to outer sidewall 310 surrounding the port in order to receive an inflation medium, via arrow C, according to some embodiments.

With reference to FIG. 3, it may be appreciated that, although, due to additional inward protruding member 33, a cross-sectional area of lumen 302 is smaller than that of lumen 102 of either of devices 100, 200, for a given diameter of devices 100, 200, 300, inward protruding member 33 can increase a stability of outer sidewall 310 by both the resulting increased wall thickness thereof, and the extension thereof between ends 225, 227 of inner sidewall 220. According to some alternate embodiments, a removable member may take the place of member 33, for example, as illustrated in FIG. 4.

Figure 4:
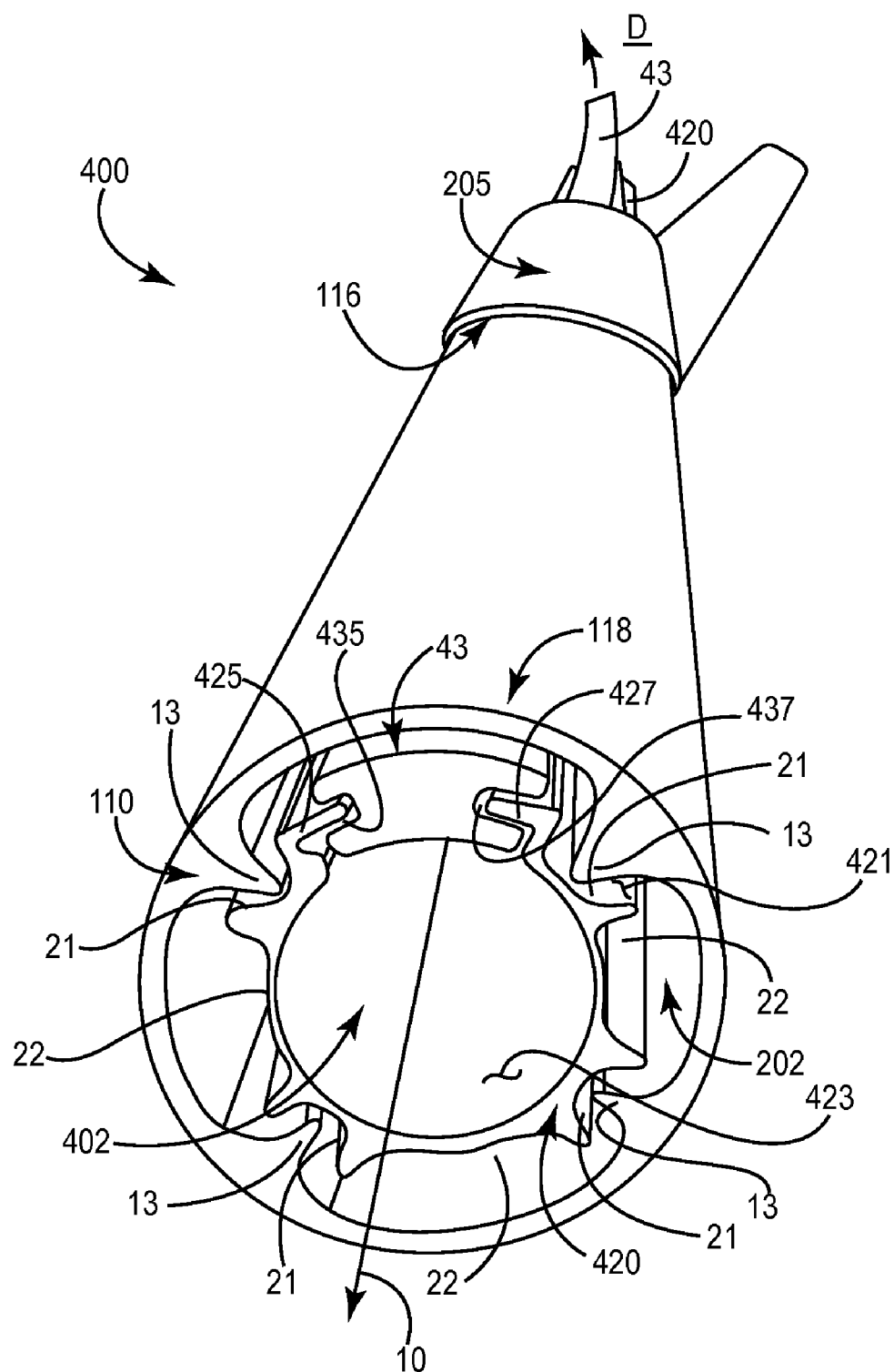
FIG. 4 is a perspective view of a delivery device.

FIG. 4 is a perspective view of a delivery device 400, according to additional embodiments of the present invention. FIG. 4 illustrates device 400 including the previously described outer sidewall 110 and an inner sidewall 420, which is similar to previously described inner sidewall 220; inner sidewall 420 differs from inner sidewall 220 in that first and second ends 435 and 427 of sidewall 420 extend toward one another to interlock with features 435 and 437, respectively, of a longitudinally extending removable support member 43. FIG. 4 further illustrates member 43 spanning the slitting zone, within outer sidewall 110 and between ends 425, 427 of inner sidewall 420, in order to prevent distortion of outer sidewall 110 during delivery of an implantable device, via a lumen 402 of delivery device 400.

According to the illustrated embodiment, support member 43 is slidably engaged within outer sidewall 110, and between ends 425, 427 of inner sidewall 420, so that, once the implantable device has been delivered through lumen 402 and implanted, member 43 may be pulled out from a proximal end of delivery device 400, per arrow D. Once member 43 is removed from device 400, outer sidewall 110 may be slit, between ends 425, 427, in order to peel device 400 away from around the implanted device. Although FIG. 4 shows inner sidewall 420 extending proximally from hub 205, the invention is not so limited, and inner sidewall 420 may be contained between hub 205 and distal end of outer sidewall 118.

Suitable materials for each of sidewalls 110 and 420, of device 400, may be selected from the groups of exemplary materials, which have been listed above for either of devices 100, 200. Support member 43 may be also be formed from any of these materials having a suitable elastic modulus, for example, that of a 55D durometer polyurethane, like Pellethane 2363-55D, and preferably from those having a relatively low coefficient of friction, for example, PEEK, PTFE, HDPE or PVDF, unless a lubricant, for example, the aforementioned Dow MDX4-4159, is employed. Alternately, support member is formed from a metal material, which is formed to be flexible enough so as not to significantly impair a trackability of device 400.

With reference back to FIG. 1A, it should be appreciated that inner sidewall 120 of device 100 may be likewise modified to interlock with support member 43, if member 43 is incorporated by device 100, according to further embodiments of the present invention. Alternatively, a support member, like member 43 may include interlocking features designed to mate with ends 125, 127 of inner sidewall 120 or with ends 225, 227 of inner sidewall 220 in either of devices 100 or 200.

Figure 5:
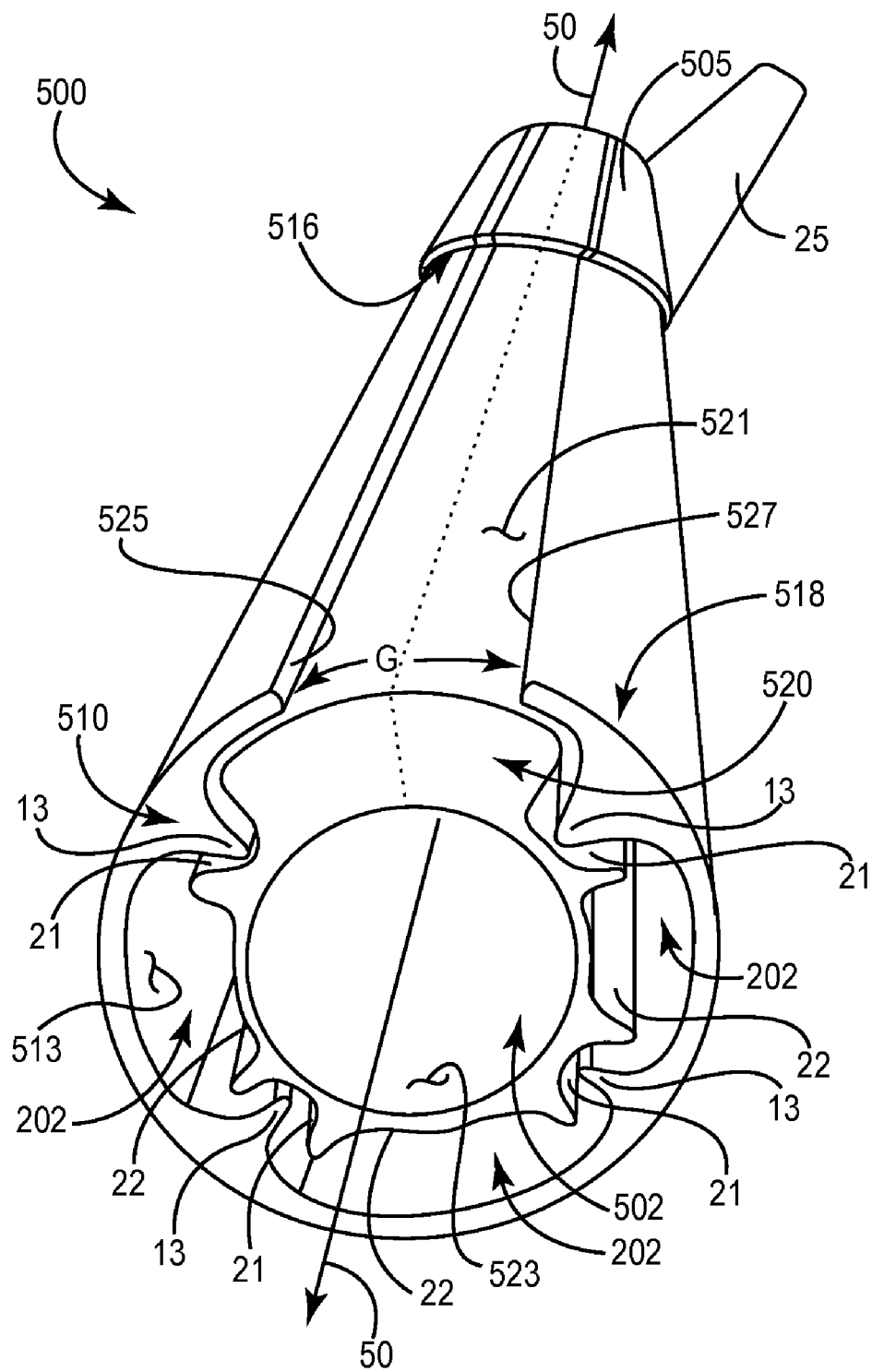
FIG. 5 is a perspective view of a delivery device.

Although not heretofore mentioned, it may be appreciated that the slitting zones for delivery devices of the present invention may be provided by a gap in an outer sidewall, as opposed to a gap in an inner sidewall. FIG. 5 is a perspective view of a delivery device 500, according to these alternate embodiments of the present invention.

FIG. 5 illustrates device 500 including an outer sidewall 510 surrounding an inner sidewall 520. Outer sidewall 510 is shown extending longitudinally from a proximal end 516 to a distal end 518 thereof, and extending, from a first end 525 to a second end 527 thereof, less than 360 degrees about a longitudinal axis 50 of device 500; and an inner sidewall 520 is shown extending within outer sidewall 510, between proximal end 516 and distal end 518, and extending 360 degrees about axis 50, thereby spanning a longitudinally extending gap G between ends 525, 527 of outer sidewall 510. According to the illustrated embodiment, an inner surface 523 of inner sidewall 520 defines a longitudinally extending lumen 502 of delivery device 500, and a slitting zone for device 500 extends along that portion of inner sidewall 520 which spans gap G, for example, as indicated with dashed lines. According to exemplary embodiments, a width of gap G is between approximately 0.01 inch and approximately 0.05 inch. Although gap G is shown extending alongside a hub 505 of device 500, which hub 505 may be attached directly to either of, or both of inner sidewall 520 and outer sidewall 510, according to alternate embodiments, hub 105 spans gap G as shown by dashed lines in FIG. 5.

FIG. 5 further illustrates inner sidewall 520 including longitudinally extending grooves 21, which are defined by an outer surface 521 of sidewall 520, and which interlock with longitudinally extending inward protruding members 13 of outer sidewall 510, which are defined by an inner surface 513 of outer sidewall 510. Although FIG. 5 shows outer surface 521 further defining a second set of grooves 22 which, together with inner surface 513 of outer sidewall 510, form additional lumens 202 of device 500, it should be understood that outer surface 521 may alternately not include grooves 22, for example, like outer surface 121 of inner sidewall 120 of device 100 (FIG. 1A), so that additional lumens 202 are not included in device 500. According to some embodiments, ends 525, 527 of outer sidewall 510 are bonded, either thermally or adhesively, to outer surface 521 of inner sidewall 520. Furthermore, these embodiments may include a relatively thin layer of adhesive potting material spanning gap G. Suitable materials for each of sidewalls 510 and 520, of device 500, may be selected from the groups of exemplary materials, which have been listed above for either of devices 100, 200.

In the foregoing detailed description, the invention has been described with reference to specific embodiments. However, it may be appreciated that various modifications and changes can be made without departing from the scope of the invention as set forth in the appended claims.

We claim:

1. An elongate medical delivery device comprising:
an outer sidewall extending from a proximal end thereof to a distal end thereof and 360 degrees about a longitudinal axis of the device, the outer sidewall including an inner surface, the inner surface defining a plurality of longitudinally extending inward protruding members of the outer sidewall, each of the plurality of inward protruding members being spaced apart from one another about the longitudinal axis;
an inner sidewall extending within the outer sidewall between the proximal and distal ends thereof and extending from a first end of the inner sidewall to a second end of the inner sidewall less than 360 degrees about the longitudinal axis of the device, the inner sidewall including an outer surface and an inner surface, the outer surface of the inner sidewall defining a plurality of longitudinally extending grooves of the inner sidewall, each of the plurality of grooves spaced apart from one another about the longitudinal axis and interlocking with a corresponding inward protruding member of the plurality of longitudinally extending inward protruding members of the outer sidewall; and
a longitudinally extending lumen defined by the inner surface of the inner sidewall and a portion of the inner surface of the outer sidewall that extends between the first and second ends of the inner sidewall, the lumen extending from a first opening in proximity to the proximal end of the outer sidewall to a second opening in proximity to the distal end of the outer sidewall.

2. The device of claim 1, wherein the portion of the inner surface of the outer sidewall is located between a pair of adjacent inward protruding members.

3. The device of claim 1, wherein:
the outer sidewall is formed from a first material and the inner sidewall is formed from a second material;
the first material is selected from the group consisting of: polyether block amides, polyurethanes, nylons, silicone rubbers, polyethylenes and polyesters; and the second material is selected from the group consisting of: polyether block amides, nylons, fluoropolymers, thermoplastic fluoropolymers, polyetheretherketones and polyethylenes.

4. The device of claim 1, wherein the inner sidewall extends proximally from the proximal end of the outer sidewall.

\* \* \* \* \*